US010029028B2

(12) United States Patent
Bufler

(10) Patent No.: US 10,029,028 B2
(45) Date of Patent: Jul. 24, 2018

(54) BIOMIMETIC COLLAGEN-HYDROXYAPATITE COMPOSITE MATERIAL

(71) Applicant: Geistlich Pharma AG, Wolhusen (CH)

(72) Inventor: Michael Bufler, Eich (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 14/903,394

(22) PCT Filed: Jul. 18, 2014

(86) PCT No.: PCT/EP2014/001966
§ 371 (c)(1),
(2) Date: Jan. 7, 2016

(87) PCT Pub. No.: WO2015/007393
PCT Pub. Date: Jan. 22, 2015

(65) Prior Publication Data
US 2016/0144071 A1 May 26, 2016

(30) Foreign Application Priority Data

Jul. 19, 2013 (EP) .................................... 13003647

(51) Int. Cl.
| A61L 27/32 | (2006.01) |
| A61L 27/24 | (2006.01) |
| A61L 27/56 | (2006.01) |
| A61L 27/54 | (2006.01) |
| A61L 27/58 | (2006.01) |

(52) U.S. Cl.
CPC ............. *A61L 27/32* (2013.01); *A61L 27/24* (2013.01); *A61L 27/54* (2013.01); *A61L 27/56* (2013.01); *A61L 27/58* (2013.01); *A61L 2300/112* (2013.01); *A61L 2300/412* (2013.01); *A61L 2400/12* (2013.01); *A61L 2400/18* (2013.01); *A61L 2420/02* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| 5,231,169 A * | 7/1993 | Constantz | ............... C07K 14/78 106/151.1 |
| 6,201,039 B1 | 3/2001 | Brown et al. | |
| 2009/0216336 A1 | 8/2009 | Springer et al. | |
| 2009/0232875 A1 | 9/2009 | Tampieri et al. | |
| 2010/0021520 A1 | 1/2010 | Baskin et al. | |
| 2012/0130506 A1* | 5/2012 | Bufler | ................. A61L 24/0063 623/23.61 |

FOREIGN PATENT DOCUMENTS

| JP | 2011526507 A | 10/2011 |
| JP | 2012530568 A | 12/2012 |

OTHER PUBLICATIONS

McAlinden, A., et al., "α-Helical Coiled-coil Oligomerization Domains are Almost Ubiquitous in the Collagen Superfamily," Journal of Biological Chemistry 278(43): 42200-42207 (2003).*
Almora-Barrios, N. and N. De Leeuw, Molecular Dynamics Simulations of the Early Stages of Nucleation of Hydroxyapatite at Collagen Template, Crystal Growth & Design 12: 756-763 (published Dec. 16, 2011).*
International Preliminary Report on Patentability issued in PCT/EP2014/001966 dated Oct. 14, 2015, 14 pages.
Intention to Grant Communication under Rule 71(3) EPC issued in European Application 14 741 205.0-1455, dated Jul. 6, 2016, 5 pages.
Ficai et al., "Self-assembled collagen/hydroxyapatite composite material", Chemical Engineering Journal, vol. 160, No. 2, 2010.
International Search Report cited in International Application No. PCT/EP2014/001966 dated Sep. 19, 2014, 3 pages.

(Continued)

*Primary Examiner* — David J Blanchard
*Assistant Examiner* — Daniel F. Coughlin
(74) *Attorney, Agent, or Firm* — Rothwell, Figg, Ernst & Manbeck, P.C.

(57) ABSTRACT

The invention relates to: —a biomimetic collagen-hydroxyapatite composite material comprising an at least partially fibrous collagen scaffold including mature native collagen fibers possessing triple helicity as shown by Circular Dichroism Spectroscopy, wherein those mature native collagen fibers are at least partially covered with epitactically grown crystals of nanocrystalline hydroxyapatite, whereby the epitactically grown nanocrystals have the same morphology as human bone mineral and the same size as human bone mineral, i.e. a length of 30 to 50 nm and a width of 14 to 25 nm, —a process of preparing the above biomimetic collagen-hydroxyapatite composite material comprising the steps of a) immersing an at least partially fibrous collagen scaffold including the above mature native collagen fibers in a saturated aqueous solution of saturated $Ca^{2+}/Hx\text{-}PO4^{(3-x)}$ to start the formation process of the composite implant material whereby epitactically grown nanocrystals will be formed on the mature native collagen fibers, the epitactically grown nanocrystals having the same morphology and same size as human bone mineral, b) stopping the formation process of the composite implant material by separating solid material from the aqueous solution, rinsing with water and drying, and c) optionally sterilizing the separated material coming from step b), as well as —the use of the above biomimetic collagen-hydroxyapatite composite material as an implant or prosthesis for bone formation, bone regeneration, bone repair and/or bone replacement at a defect site in a human subject or in an animal, or as an implant for combined bone and cartilage regeneration.

17 Claims, 3 Drawing Sheets

(56) References Cited

OTHER PUBLICATIONS

Figure 1:
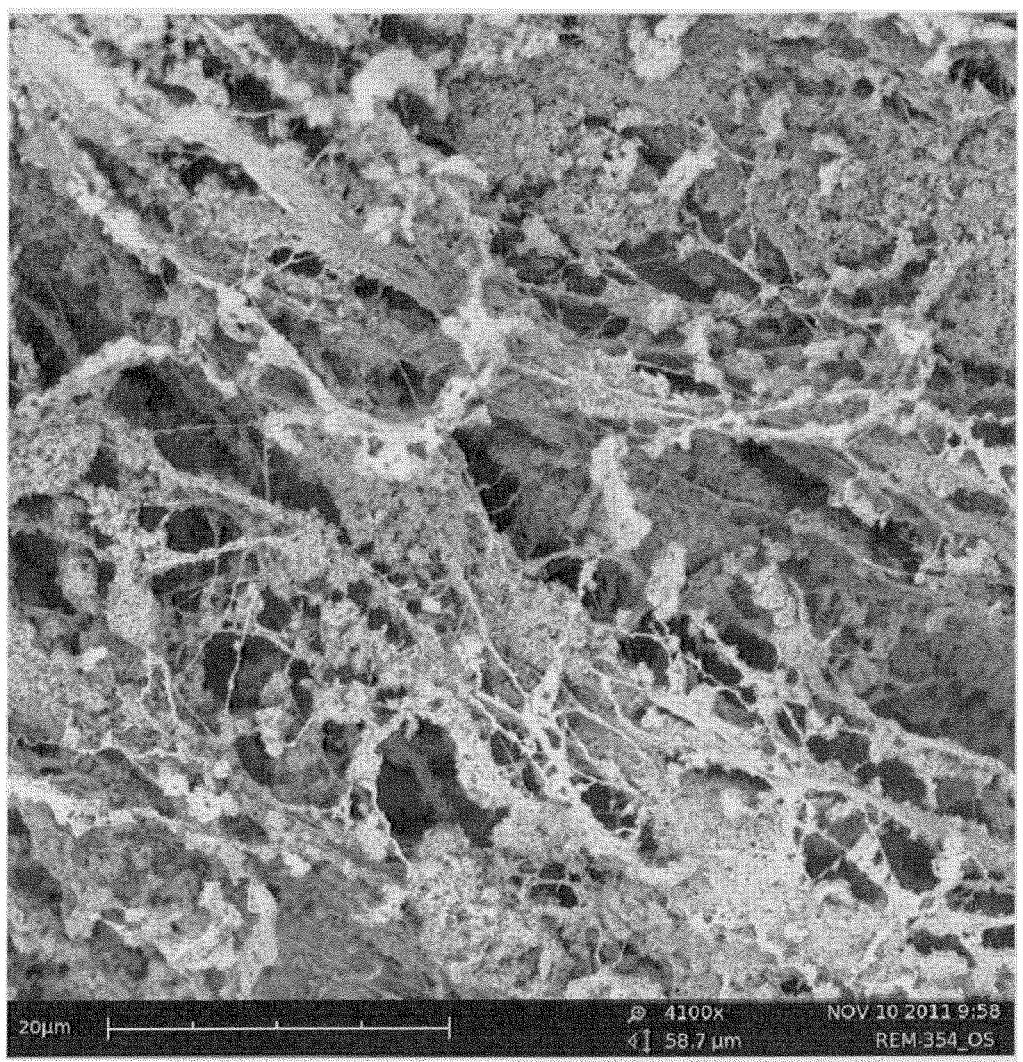

English translation of Notice of Grounds of Rejection cited in Japanese Patent Application No. 2016-526468, dated Mar. 27, 2018, 4 pages.
English translation of Office Action in Russian Patent Application No. 2016 105 556, dated Feb. 12, 2018, 5 pages.

* cited by examiner

BIOMIMETIC COLLAGEN-HYDROXYAPATITE COMPOSITE MATERIAL

CROSS REFERENCE TO RELATED APPLICATION

This application is a 35 U.S.C. 371 National Phase Entry Application from PCT/EP2014/001966, filed Jul. 18, 2014, which claims the benefit of European Patent Application No. 13003647.8, filed on Jul. 19, 2013, the disclosures of which are incorporated by reference in their entireties.

The invention relates to a new biomimetic collagen-hydroxyapatite composite material comprising an at least partially fibrous collagen scaffold and hydroxyapatite, wherein the collagen fibers are at least partially covered with epitactically grown crystals of nanocrystalline hydroxyapatite, a process for preparing that material and the use thereof as an implant to support bone formation, bone regeneration, bone repair and/or bone replacement at a defect site in a human subject or an animal, or as an implant for combined bone and cartilage regeneration.

Defects in bone structure arise in a variety of circumstances, such as trauma, disease, and surgery and there is still a need for effective repair of bone defects in various surgical fields. Numerous natural and synthetic materials and compositions have been used to stimulate healing at the site of a bone defect.

A well-known natural, osteoconductive bone substitute material that promotes bone growth in periodontal and maxillofacial osseous defects or osseous defects in the orthopedic field is Geistlich Bio-Oss® or Geistlich Orthoss, respectively, commercially available from Geistlich Pharma AG. That hydroxyapatite based bone mineral material is manufactured from natural bone by a process described in U.S. Pat. No. 5,167,961, which enables preservation of the trabecular architecture and nanocrystalline structure of the natural bone.

Hydroxyapatite based materials are however not always adapted to repairing large bone defects, notably in orthopedics, being brittle and not sufficiently resistant to mechanical stresses to be screwable, e.g. on an osseous body part.

There is thus a need for a synthetic or partially synthetic bone graft material made to closely resemble natural bone, notably in its resistance to mechanical stresses. Such a biomimetic synthetic or partly synthetic bone graft material would for certain applications, notably for repairing large bone defects, be a useful replacement of bone grafts derived from natural bone.

Natural bone is a composite material consisting of water and a collagenous matrix consisting mainly of type I collagen, which is intimately combined with inorganic crystals, principally of hydroxyapatite. Collagen type I fibers and hydroxyapatite account for approximately w/w 25 to 30% and w/w 65 to 70% of the natural bone dry weight, respectively. The collagenous matrix gives bone its flexibility and resilience while the inorganic material gives bone its strength and rigidity, the organization of the two phases providing a high degree of elasticity and toughness of the composite. A thorough review of bone structure from the angstrom level (mineral crystal) to the micron level (lamellae) has been presented by Weiner, S. et al., 1992, FASEB, 6:879-885.

One important feature of natural bone is the morphology and the very small size of the hydroxyapatite crystals, which for human bone mineral is: hexagonal space group $P6_3/m$, about 30 to 50 nm in length (c axis: [0,0,1]) and 14 to 25 nm in (a and b axes: [1,0,0] and [0,1,0]). See Weiner S. et al. cited above.

N. A. Barrios et al. in "Density Functional Study of Binding of Glycine, Proline and Hydroxyproline to the Hydroxyapatite (0001) and (01 $\bar{1}$0) Surfaces", 2009, Langmuir 25(9), 5018-5025 and "Molecular Dynamics Simulation of the Early Stages of Nucleation of Hydroxyapatite at a Collagen Template", Crystal Growth Design, 2012, 12, 756-763, show that at human body temperature the nucleation and coupling of hydroxyapatite to the collagen fibers can take place at different sites of the collagen amino acid building blocks glycine, proline and hydroxyproline, namely on the crystal surface (0001) and (01 $\bar{1}$0), coupling on the crystal surface (01 $\bar{1}$0) being preferred. This proves that in the human body the structure of the collagen fiber and its amino acids building blocks provides a substrate exactly corresponding to the crystal structure of hydroxyapatite, therefore bone formation follows an epitactic growth pathway to interconnect the hydroxyapatite crystals and the collagen fibers. The epitactic growth pathway is thermodynamically favored yielding the lowest energy configuration.

Attempts have been made in the prior art to provide collagen-hydroxyapatite composite materials which are similar to natural bone.

U.S. Pat. No. 5,231,169 describes a method of mineralizing collagen with a calcium phosphate mineral which comprises preparing said calcium phosphate mineral in the presence of a dispersion of dispersed collagen fibrils in basic aqueous solution having a pH in the range 10-13, adding to said dispersion over a period at least one hour a source of soluble calcium and soluble phosphate in the correct ratio such as to produce said phosphate mineral, and collecting the mineralized collagen. Mineralized collagen with stably distributed calcium phosphate in the collagen matrix is taught to be thus obtained.

U.S. Pat. No. 5,739,286 discloses a method of making a bone augmentation material resembling natural bone by mineralizing collagen fibers over a 7-day period in a double diffusion chamber, one reservoir containing 0.05 M tris buffer and 0.1 M calcium chloride and the other reservoir containing 0.05 M tris buffer and 0.1 M potassium phosphate. A calcium phosphate precipitate is taught to be formed on the collagen fibers, scanning electron micrographs of the mineralized collagen fibers being morphologically similar to plate-like aggregates of hydroxyapatite found precipitated on bioglass materials soaked in synthetic blood plasma.

U.S. Pat. Nos. 6,395,036 and 6,589,590 describe a method of making artificial bone by providing a collagen membrane with solutions of calcium ions and of phosphate ions on opposite sides of the membrane, those ions diffusing through the membrane, meeting and precipitating as a hydroxyapatite material inside the collagen membrane.

U.S. Pat. Nos. 7,514,249 and 7,547,449 disclose a method of making a biomimetic collagen sponge mineralized with calcium phosphate, wherein the calcium phosphate is embedded in the interstitial spaces of the collagen fibrils, by using a solution of 6 mM calcium chloride and 200 µg/ml of both poly (alpha beta-DL-aspartic acid) and poly (vinyl phosphonic acid), followed by vapor diffusion of ammonium phosphate dibasic.

Ficai A. et al., 2010, Chemical Engineering 160, 794-800 discloses a process of preparing a collagen-apatite composite material starting from a collagen gel and hydroxyapatite precursors where the pH is adjusted at about 9 using a sodium hydroxide solution such as to ensure hydroxyapatite precipitation and fibrillogenesis. Crystals of hydroxyapatite are thus formed "in the nanometer range, between a few nanometers and up to 40 nm". Since nucleation of hydroxyapatite takes place during fibrillogenesis, during which self-assembling of the collagen molecules changes the positions of the aminoacid building blocks of collagen (which hence do not correspond exactly to the crystal structure of hydroxyapatite), there cannot be any epitactic growth of the hydroxyapatite crystals: Those crystals are precipitated as stated in that publication.

Patent Publication US 2009/0232875 describes a multilayer structure comprising a first upper layer consisting of an organic matrix containing collagen and at least a lower layer of a composite matrix containing hydroxyapatite and collagen (paragraph [0001]). The composite is obtained by a direct nucleation process of hydroxyapatite on self-assembling collagen fibrils at a pH of 9-11 and a temperature of 35 to 40° C., the sizes of the crystals being 12-15 nm along the fiber axis (paragraphs [0082] and [0089]). Since, like in Ficai et al. above, nucleation of hydroxyapatite takes place during self-assembling of the collagen molecules (the latter changing the positions of the aminoacid building blocks of collagen) and furthermore this nucleation "involves a carbonation of the inorganic phase, i.e. incorporation of $CO_3^{2-}$ groups on the hydroxyapatite lattice" (see paragraph [0077], lines 25-28), carbonated hydroxyapatite having a different crystal structure (Monoclinic crystal structure with space group Pb or $P2_1/b$: See Elliot J. C. 1994: Structure and Chemistry of the Apatites and Other Calcium Phosphates. Studies in inorganic Chemistry 18. Elsevier Science, ISBN 0-444-81582-1), there cannot be any epitactic growth of the hydroxyapatite crystals: Those crystals grow therefore by precipitation on the "nano-nuclei formed within the collagen fibril . . . parallel to the fibrils" (see paragraph [0090]).

In the collagen-hydroxyapatite composite materials of the prior art the hydroxyapatite is precipitated on or inside the collagen scaffold, the link with the latter being only a weak physical link, e.g. by adsorption. Such a weak physical link is not capable of providing the material with the elasticity, resistance to torque and toughness of natural bone in which the hydroxyapatite crystals are epitactically grown on the collagen fibers.

An objective of the invention is thus to provide a biomimetic collagen-hydroxyapatite composite wherein there is a strong link between the collagen scaffold and the hydroxyapatite crystals.

In the collagen-hydroxyapatite composite materials of the prior art the hydroxyapatite crystals do not have the morphology (crystal face ratio and lattice parameters) and the very small size of natural bone mineral, in particular human bone mineral.

Another objective of the invention is thus to provide a biomimetic collagen-hydroxyapatite composite wherein the collagen crystals have the same morphology and same size as human bone mineral.

European Patent No. 2'445'543 teaches the conditions under which nanocrystals of hydroxyapatite epitactically grow on a sintered α-TCP core, those nanocrystals having the same morphology and same size as human bone mineral.

It has been found that the above objectives can be attained by adapting the conditions described in European Patent No. 2'445'543 for epictactically growing nanocrystals of hydroxyapatite on collagen fibers, those nanocrystals having the same morphology and same size as human bone mineral.

A biomimetic collagen-hydroxyapatite composite material is thus obtained with excellent mechanical properties, notably a high resistance to mechanical stress, in particular a high resistance to torque (at least 30 Ncm, generally about 60 Ncm), thanks to the strong epitactic binding between the collagen scaffold and the hydroxyapatite crystals. This material upon implantation in a human body is readily colonized by bone-forming cells and shows excellent osteoconductivity and osseointegration properties thanks notably to the fact that the hydroxyapatite crystals have the same morphology and same size as human bone mineral.

The above objectives are attained by the invention as defined in the appended claims.

The invention thus concerns a new biomimetic collagen-hydroxyapatite composite material comprising an at least partially fibrous collagen scaffold including mature native collagen fibers possessing triple helicity as shown by Circular Dichroism Spectroscopy, wherein those mature native collagen fibers are at least partially covered with epitactically grown crystals of nanocrystalline hydroxyapatite, whereby the epitactically grown nanocrystals have the same morphology as human bone mineral and the same size as human bone mineral, i.e. a length of 30 to 50 nm and a width of 14 to 25 nm.

The term "the same morphology as human bone mineral" means that the dimensional relationship of the crystal faces (which determines the external shapes of crystals) is the same as in human bone mineral. In the latter the crystals are generally hexagonal platelets.

Epitactic growth of hydroxyapatite on collagen can only take place on fibers of collagen, as shown by the publications of N. A. Barrios et al. cited above. Such fibers must be mature native collagen fibers, i.e collagen fibers where (a) the fibrils have been assembled by self assembling of the collagen building blocks, (b) the alpha 1 and alpha 2 chains have been formed and (c) the triple helix has been formed by natural crosslinking of two alpha 1 chains with one alpha 2 chain. Such mature native collagen fibers possess triple helicity as shown by Circular Dichroism Spectroscopy. On mature native collagen fibers the respective positions of the collagen building blocks glycine, proline and hydroxyproline are fixed, exactly corresponding to the structure of hydroxyapatite, thus enabling the epitactic interconnection between hydroxyapatite and the mature native collagen fibers. Fibers in formation where the fibrils self-assembling, the alpha 1 and alpha 2 chains are forming or the triple helix is forming are not appropriate for epitactic growth of hydroxyapatite. Indeed, in such fibers in formation the positions of the building blocks of collagen change, thus not exactly corresponding to the crystal structure of hydroxyapatite.

It is thus necessary that the collagen scaffold is at least partially fibrous on its external surface and includes mature native collagen fibers possessing triple helicity as shown by Circular Dichroism Spectroscopy.

The at least partially fibrous collagen scaffold generally comprises on its external surface at least 2% of mature native collagen fibers, preferably at least 5% mature native collagen fibers, more preferably at least 10% mature native collagen fibers, as determined by picture analysis on SEM micrographs and Circular Dichroism Spectroscopy.

The at least partially fibrous collagen scaffold is generally composed of type I collagen but may also include other types of collagen, notably type II and type III collagen.

The at least partially fibrous collagen scaffold is generally a collagen matrix derived from a natural material or a semi-artificial or artificial collagen matrix, e.g. prepared by electrospinning from a suspension of collagen particles or a solution of soluble collagen, the collagen being derived from a natural material or being recombinant collagen.

The epitactically grown crystals of nanocrystalline hydroxyapatite usually form a layer having a thickness of at least 30±15 nm, as determined by X-ray diffraction analysis. The thickness of at least 30±15 nm corresponds to one layer of hydroxyapatite nanocrystals in epitaxial orientation.

The epitactically grown layer of nanocrystalline hydroxyapatite may comprise a single or multiple layers of hydroxyapatite nanocrystals in epitaxial orientation to the collagen fibers substrate. The thickness of the epitactically grown layer of nanocrystalline hydroxyapatite, which is related to the number of such layers of hydroxyapatite nanocrystals in epitaxial orientation, will be selected according to the intended application of the bone substitute material as an implant in the human body.

The thickness of the epitactically grown layer of nanocrystalline hydroxyapatite is related to the w/w ratio of the fibrous collagen scaffold to the epitactically grown crystals of nanocrystalline hydroxyapatite, said ratio being generally is between 5:95 and 95:5, preferably between 10:90 and 90:10, more preferably between 20:80 and 60:40, in particular between 30:70 and 70:30.

The biomimetic collagen-hydroxyapatite composite material may be a particulate or a granulate, the particles or granules having a desired size and shape. Generally the particles or granules are approximately spherical and have a diameter of 20 to 5000 μm.

The biomimetic collagen-hydroxyapatite composite material may also be a shaped body of any shape, e.g. a cubic or parallelepipedic block, a plate, a cylinder, a tapered key, a nail, a screw, a pin or a structure having the profile of an osseous body part such as notably a hip, a clavicle, a rib, a mandible or a skull part. Such shaped body may have a sufficient resistance to torque to be screwable, e.g. on an osseous body part, i.e. a resistance to torque of at least 30 Ncm in the dry state, preferably a resistance to torque of at least 50 Ncm in the dry state.

The biomimetic collagen-hydroxyapatite composite material may also be a membrane shaped body.

A suitable collagen scaffold for a membrane shaped body is the Bio-Gide® membrane (Geistlich Pharma A. G., Switzerland) manufactured according to the process described in EP-B1-1676592, which has a fibrous side allowing bone-forming cells ingrowth and a smooth side acting as barrier against non-bone-forming cells ingrowth. Such a membrane will generally be coated only on the fibrous side with epitactically grown hydroxyapatite nanocrystals, thereby providing on that side very favourable conditions for bone formation.

The biomimetic collagen-hydroxyapatite composite material of the invention may be used as an implant or prosthesis for bone formation, bone regeneration, bone repair and/or bone replacement at a bone defect site, notably a large bone defect site, in a human subject or an animal.

The invention thus also concerns:
the use that biomimetic collagen-hydroxyapatite composite material as an implant or prosthesis for bone formation, bone regeneration, bone repair and/or bone replacement at a defect site in a human subject or an animal and
a method of promoting bone formation, bone regeneration and/or bone repair at a defect site in a human subject or an animal by implanting a biomimetic collagen-hydroxyapatite composite material.

A membrane-shaped body of biomimetic collagen-hydroxyapatite composite material of the invention wherein only one side is coated with epitactically grown hydroxyapatite nanocrystals may be used as an implant for combined bone and cartilage regeneration, the coated side being oriented such that it faces the bone defect and the non-coated side being oriented such that it faces the cartilage defect.

The invention thus also relates to the use of a membrane-shaped body of biomimetic collagen-hydroxyapatite composite material as an implant for combined bone and cartilage regeneration.

The invention further relates to a process for preparing the above defined biomimetic collagen-hydroxyapatite composite material comprising the steps of:

a) immersing an at least partially fibrous collagen scaffold including mature native collagen fibers possessing triple helicity as shown by Circular Dichroism Spectroscopy in a saturated aqueous solution of saturated $Ca^{2+}/H_xPO_4^{(3-x)}$ to perform the formation process of the composite implant material, whereby epitactically grown hydroxyapatite nanocrystals are formed on those mature native collagen fibers, the epitactically grown nanocrystals having the same morphology and same size as human bone mineral, b) stopping the formation of epitactically grown hydroxyapatite nanocrystals by separating solid material from the aqueous solution, rinsing with water and drying, and c) optionally sterilizing the separated dried material coming from step b).

The at least partially fibrous collagen scaffold is generally a collagen matrix derived from a natural material or a semi-artificial or artificial collagen matrix, which has a pre-shape compatible with the desired final shape for the biomimetic composite material and a degree of crosslinking sufficient for the desired mechanical properties of the biomimetic composite material. If necessary, the preparation of that collagen scaffold will include a step to give it the desired pre-shape and a crosslinking step to give it a sufficient cohesion and toughness.

Before performing step a) the at least partially fibrous collagen scaffold is generally cleaned in an alcohol such as e.g. ethanol and isopropanol and an ether such as e.g. diethylether.

The saturated aqueous solution of saturated $Ca^{2+}/H_xPO_4^{(3-x)}$ may be a phosphate buffer solution (PBS) containing finely dispersed alpha-TCP, beta-TCP, TTCP, octacalcium phosphate pentahydrate, dicalcium phosphate or dicalcium phosphate dihydrate. Such a dispersion of a calcium phosphate in a PBS solution allows that solution to remain saturated in $Ca^{2+}/H_xPO_4^{(3-x)}$ when $Ca^{2+}$ and $H_xPO_4^{(3-x)}$ ions are consumed to form hydroxyapatite.

The saturated aqueous solution of saturated $Ca^{2+}/H_xPO_4^{(3-x)}$ may also be a phosphate buffer solution to which $Ca^{2+}$ and $H_xPO_4^{(3-x)}$ ions are added to compensate for their consumption in forming hydroxyapatite, e.g. by dripping a solution containing such ions into the reaction medium.

The phosphate buffer solution has generally a concentration from 0.1 to 1.0 M, in particular from 0.2 to 0.8 M.

The pH of the saturated aqueous solution of saturated $Ca^{2+}/H_xPO_4^{(3-x)}$ usually remains during step a) within a range of 5.5 to 9.0, preferably 6.5 to 8.0.

Step a) is generally performed at temperature between 25 and 45° C., preferably between 35° C. and 42° C.

Step a) is performed for a sufficient time such as to allow epitactic growth of substantive amounts of hydroxyapatite crystals on the mature native collagen fibers. Epitactic growth is indeed thermodynamically favored yielding the lowest energy configuration but it takes time to be established. Generally such a sufficient time is at least about 12 hours, preferably at least about 24 hours.

Those conditions of step a), close to the bone-forming conditions in the human body, allow epitactic growth on collagen fibers of hydroxyapatite nanocrystals having the same morphology and size as human bone mineral.

Step a) is generally carried out for a time at least sufficient such that a closed coating of at least one nanocrystalline layer of hydroxyapatite is present on the mature native collagen fibers: That time is chosen according to the properties desired for the biomimetic collagen-hydroxyapatite material, in a particular the desired number of nanocrystalline layers and w/w ratio of the collagen scaffold to the epitactically grown layers of nanocrystalline hydroxyapatite.

In step b) the formation of epitactically grown hydroxyapatite nanocrystals is stopped by separating solid material from the aqueous solution, rinsing with water and drying.

Generally a further optional step c) of sterilizing the separated dried material coming from step b) is performed.

Advantages of the Biomimetic Collagen-Hydroxyapatite Composite Material of the Invention Thanks to the strong epitactic linking, as in natural bone, between the collagen scaffold and the hydroxyapatite nanocrystals, the synthetic or partially synthetic biomimetic collagen-hydroxyapatite composite material of the invention has excellent mechanical properties, notably a high resistance to mechanical stress, in particular a high resistance to torque (at least 30 Ncm, generally about 60 Ncm), a high compressive strength and a high resilience. Thanks to those excellent mechanical properties, shaped bodies of the biomimetic collagen-hydroxyapatite composite material of the invention are screwable, notably on osseous body parts, and also permanently keep volume under mechanical stress: They are thus ideally adapted to repairing large bone defects.

The biomimetic collagen-hydroxyapatite composite material of the invention is readily colonized by bone forming cells with a low level of cytotoxicity (see Example 4 d) below) and shows excellent osteoconductivity and osseointegration properties in the human body, thanks notably to the fact that the hydroxyapatite nanocrystals have the same morphology and the same size as human bone mineral, as shown by following table 1:

TABLE 1

Comparison of the hydroxyapatite crystal size and morphology for the Sbiomimetic composite implant material of the invention and human bone mineral

| Crystallographic axes (hexagonal space group P63/m) | Biomimetic collagen-hydroxyapatite composite material of the invention prepared at physiological pH and temperature. Crystal size+ [nm] | natural human bone mineral Crystal size+ [nm] |
| --- | --- | --- |
| a (1, 0, 0) | 18 (±4) | 14-25 |
| b (0, 1, 0) | 18 (±4) | 14-25 |
| c (0, 0, 1) | 38 (±8) | 30-50 |

+Crystal size analysis has been performed by using TEM (transmission electron microscopy) as well as refinement of X-ray diffraction data by using the Bragg method and the Warren-Averbach technique.

The following examples illustrate the invention without limiting its scope.

Figure 2:
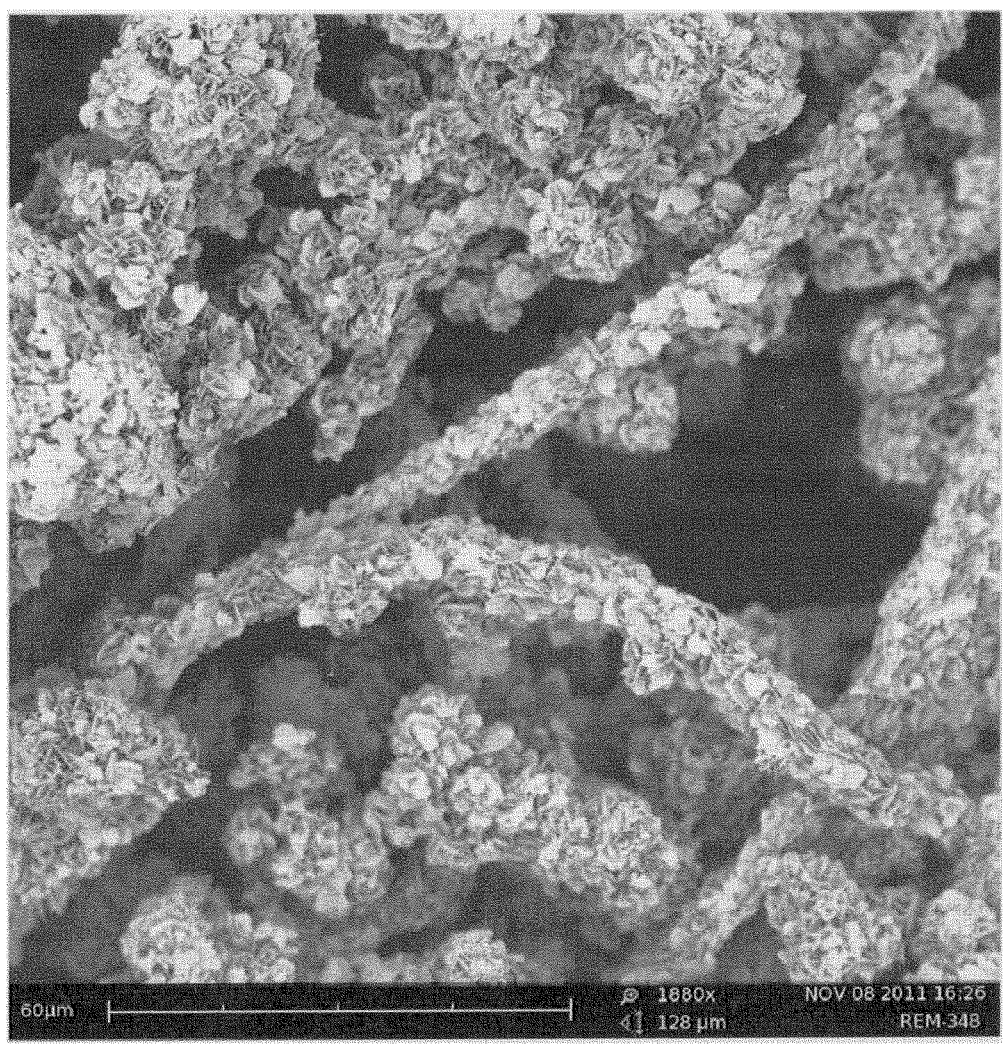
Figure 3:
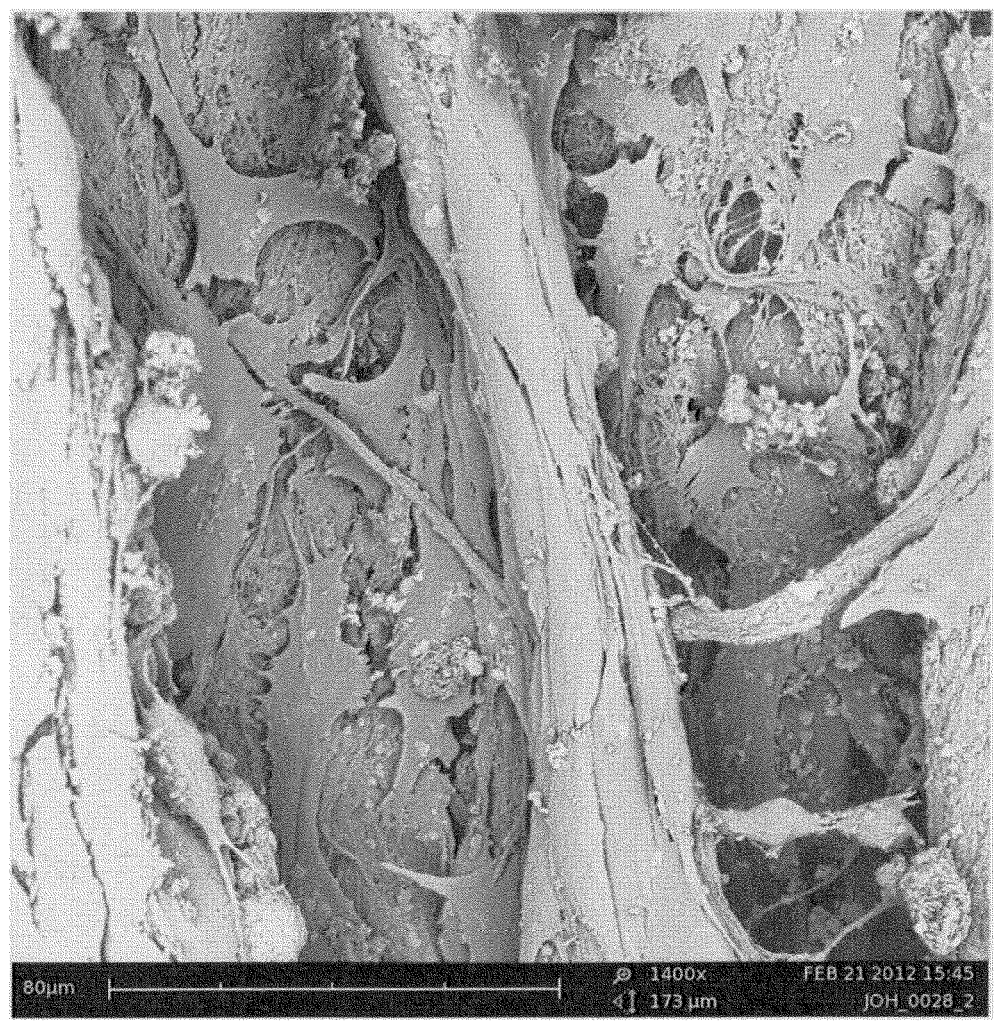

The following description will be better understood by referring to:

FIG. 1 which represents a SEM micrograph of the fibrous side of the membrane-shaped collagen scaffold of Example 1c) coated as described in Example 3 b) with a PBS concentration of 0.2 M for a coating reaction time of 12 hours, FIG. 2 which represents a SEM micrograph of the fibrous side of the membrane-shaped collagen scaffold of Example 1c) coated as described in Example 3 b) with a PBS concentration of 0.8 M for a coating reaction time of 24 hours, and FIG. 3 which represents a SEM micrograph of the fibrous side of the membrane-shaped collagen scaffold of Example 1c) coated as described in Example 3 b), which has been colonized with MG63 osteoblast-like cells.

EXAMPLE 1

Preparation of an at Least Partially Fibrous Collagen Scaffold a) Preparation of a Cylindrical Fibrous Collagen Scaffold Derived from Bio-Gide®

Preparation of Cylindrical Pieces of Dried Compacted Collagen

A Bio-Gide® membrane (Geistlich Pharma A. G., Switzerland) was finely grinded using an ultracentifugal mill and sieved on a 2.0 mm sieve. 0.2 g of the sieved collagen was put into 5 ml of 99.9% ethanol and the collagen mass was put with tweezers into a well of a 24-well plate and compacted with a 2.0 mm diameter Teflon cylinder, then extracted from the well with a 2.0 mm diameter swage tool and dried for 4 hours in a chemistry hood. Those operations were performed in parallel 6 times such as to obtain 6 cylindrical pieces of dried compacted collagen.

Crosslinking of the Cylindrical Pieces of Dried Compacted Collagen 3.571 ml of an EDC (1-Ethyl-3-[3-dimethylaminopropyl] carbodiimide hydrochloride)ethanol solution were pipetted into a 100 ml volumetric flask and the volume was completed to 100 ml with 99.9% ethanol, then poured into a 200 ml extraction flask to which the 6 pieces of dried collagen obtained above were added. The ethanol was evaporated during 1 minute under vacuum in a desiccator, then the desiccator was put to atmospheric pressure. The mixture was crosslinked under agitation at 110 rpm for 10 minutes using a horizontal shaker. The EDC solution was decanted and the collagen cylinders were put into a 200 ml beaker to which 100 ml PBS (Phosphate Buffer Solution) were added and eliminated for 1 minute under vacuum. The collagen cylinders were cleaned with 100 ml PBS under agitation at 50 rpm for 5 minutes, the PBS being decanted without evaporating under vacuum. This process was repeated 2 times. The collagen cylinders were cleaned with 100 ml 99.9% ethanol under agitation at 50 rpm for 5 minutes and the ethanol being decanted without evaporation under vacuum, the process being repeated two times. The collagen cylinders were cleaned with 100 ml diethylether without agitation and dried for 14 hours in a chemistry hood.

Other experiments were performed with a different time (up to 240 minutes) for the crosslinking reaction.

The % of mature native collagen fibres possessing triple helicity (as shown by Circular Dichroism spectroscopy) of the cylindrical collagen scaffold, as determined by picture analysis using software Phenom Pro (FEI Phenom Pro Tabletop SEM S/N: 0342; Phenom Pro Suite V.1.1.0.920; Phenom Application System PW-220-001; Phenom Fribremetric PW-210-001, available from Phenom World, Dillenburgstraat 9E, 5652 AM Eindhoven, Netherlands) on SEM (Scanning Electron Microscopy) micrographs of 5000 magnification, was about 90%.

b) Preparation of a Cylindrical Partially Fibrous Spongious Collagen Scaffold Derived from a Sponge of Type I and Type II Collagen
Preparation of a Collagen Sponge:

A resorbable extracellular spongious collagen matrix was prepared from frozen cartilage of freshly slaughtered pigs by defatting followed by basic and acidic treatment as described in Example 1 of EP-B1-810888. That matrix was shown by immunological methods to contain a mixture of type I and type II collagen.
Preparation of Cylindrical Pieces of Dried Compacted Spongious Collagen The spongeous matrix was finely grinded using an ultra-centifugal mill and sieved on a 2.0 mm sieve. 0.2 g of the sieved collagen was put into 5 ml of 99.9% ethanol and the collagen mass was put with tweezers into a well of a 24-well plate and compacted with a 2.0 mm diameter Teflon cylinder, then extracted from the well with a 2.0 mm diameter swage tool and dried for 4 hours in a chemistry hood.
Crosslinking of the Cylindrical Pieces of Dried Compacted Spongious Collagen The cylindrical pieces of dried compacted spongious collagen obtained above were crosslinked with EDC, cleaned with PBS, ethanol and diethylether, analogously to the procedure described above in a) for the fibrous cylindrical collagen scaffold. The % of mature native fibres possessing triple helicity in the cylindrical partially fibrous spongious collagen scaffold, as determined by picture analysis software Phenom Pro on SEM micrographs of 5000 magnification, was about 5%.

c) Preparation of a Membrane-Shaped Fibrous Collagen Scaffold Derived from Bio-Gide®

A Bio-Gide® membrane (Geistlich Pharma A. G., Switzerland) was cleaned with 100 ml 99.9% ethanol under agitation at 50 rpm for 5 minutes and the ethanol being decanted without evaporation under vacuum, the process being repeated two times. The collagen membrane was then cleaned with 100 ml diethylether without agitation and dried for 14 hours in a chemistry hood.

The % of mature native fibres possessing triple helicity in the fibrous side, as determined by picture analysis software Phenom Pro on SEM micrographs of 5000 magnification, was about 100%.

EXAMPLE 2

Preparation of a Bulk Sintered Material of α-TCP

For a mixture of 500 g (dry weight), 360 g dicalcium phosphate anhydrous powder, 144 g calcium carbonate powder and 220 ml deionized water were mixed for 7 minutes at 500 rpm using a laboratory stirrer. The slurry from the mixing process was immediately transferred into a high temperature stable platinum cup. The filled platinum cup was placed in a cold furnace. The furnace was heated to 1400° C. by using a heating rate of 60° C. per hour. The heating process was stopped after 72 hours by switching off the furnace. The sample was cooled down to room temperature within the furnace. The bulk sintered material (phase pure $\alpha$-$Ca_3(PO_4)_2$) was removed from the furnace and the platinum cup. The bulk product from the sintering process had a weight of 420 g (weight loss 16.7%).

The control of phase purity was performed using powder X-ray diffraction analysis.

EXAMPLE 3

Coating of a Fibrous Collagen Scaffold with Epitactically Grown Crystals of Nanocrystalline Hydroxyapatite in a PBS Solution in the Presence of a Dispersion of Fine Particles of α-TCP a) Coating of the Cylindrical Pieces of Fibrous Collagen Obtained in Example 1 a) Preparation of a 0.5 M PBS Solution:

100 ml of a 0.5 M $NaH_2PO_4.H_2O$ solution (solution A) were prepared by dissolving 6.9 g of $NaH_2PO_4.H_2O$ in sterile deionized water at room temperature under agitation at 250 rpm for 30 minutes and at 600 rpm for 4 hours. 100 ml of a 0.5 M $Na_2HPO_4.2H_2O$ solution (solution B) were prepared by dissolving 8.9 g of $Na_2HPO_4.2H_2O$ in sterile deionized water at room temperature under agitation at 250 rpm for 30 minutes and at 600 rpm for 4 hours.

19 ml of solution A were mixed with 81 ml of solution B such as to give a 0.5 M PBS solution having a pH between 7.3 and 7.4.
Crushing of α-TCP into Fine Particles:

The bulk product from Example 2 was crushed by using a jaw crusher (slot size 4 mm) The course granules were sieved by using a sieving machine and sieve inserts with mesh aperture 2 mm and 0.25 mm. The sieved granules were furthermore milled using a planet mill to a final size of less than 10 μm.
Coating of the Fibrous Collagen Cylinders Obtained in Example 1 a) with Epitactically Grown Crystals of Nanocrystalline Hydroxyapatite:

5 g of fine particles of α-TCP and 100 ml of a 0.5 M PBS solution obtained as described above and the fibrous collagen cylinders obtained in Example 1 a) were added to a glass weighing bottle which was put into a desiccator under vacuum for 5 minutes, then at atmospheric pressure. The coating reaction was performed under agitation at 37° C. during 3 days by putting the bottle on a horizontal shaker operated at 5-50 rpm in a thermostatic compartment.

Visual observation showed that the collagen scaffold retained its cylindrical shape but was covered with a white crystalline substance.
Other Experiments of Coating the Fibrous Collagen Cylinders Obtained in Example 1 a)

Other experiments of coating of the fibrous collagen cylinders obtained in Example 1 at the end of a) were performed varying the concentration of the PBS solution from 0.2 M to 0.8 M and the coating reaction time from 12 hours to 4 days.

Visual observation showed that the collagen scaffold retained its cylindrical shape but was covered with a white crystalline substance.

SEM analysis showed that crystal growth as well as the size, morphology and habitus of the hydroxyapatite crystal assemblies could be controlled by varying the concentration of the PBS solution and the coating reaction time.

In the above experiments the w/w ratio of the fibrous collagen scaffold to the epitactically grown crystals of nanocrystalline hydroxyapatite in the coated fibrous collagen cylinders was from 90/10 to 30/70.

b) Coating of the Cylindrical Partially Fibrous Spongeous Collagen Scaffold Obtained in Example 1) b) and the Membrane Shaped Fibrous Collagen Scaffold Obtained in Example 1 c) with Epitactically Grown Crystals of Nanocrystalline Hydroxyapatite:

Experiments of coating the cylindrical partially fibrous collagen sponge cylinders obtained in Example 1 b) or coating the fibrous side of the membrane-shaped fibrous collagen scaffold of Example 1c), were performed varying the concentration of the PBS solution from 0.2 M to 0.8 M and the coating reaction time from 12 hours to 4 days.

Visual observation showed that the collagen scaffold retained its shape but was covered with a white crystalline substance.

SEM analysis showed that crystal growth as well as the size, morphology and habitus of the hydroxyapatite crystal assemblies can be controlled by varying the concentration of the PBS solution and the coating reaction time.

In the above experiments the w/w ratio of the fibrous collagen scaffold to the epitactically grown crystals of nanocrystalline hydroxyapatite was from 90/10 to 30/70 for the coated partially fibrous collagen sponge cylinders obtained in Example 1b) and from 90/10 to 50/50 for the coated membrane-shaped collagen scaffold.

EXAMPLE 4

Properties of the at Least Partially Fibrous Collagen Scaffold Coated with Epitactically Grown Crystals of Nanocrystalline Hydroxyapatite a) Physicochemical Properties:

The measured porosity (pore volume) was 96 v/v % for the cylindrical pieces of fibrous collagen obtained in Example 1a) (varying the crosslinking conditions) and 85 to 95% v/v for the hydroxyapatite coated cylindrical pieces obtained in Example 3)a).

The specific surface measured by mercury porosimetry was 1.5 to 2.5 $m^2/g$ for the cylindrical pieces of fibrous collagen obtained in Example 1a) (varying the crosslinking conditions) and from 20 to 60 $m^2/g$ for the hydroxyapatite coated cylindrical pieces obtained in Example 3)a).

The measured porosity (pore volume) was about 96% v/v % for the collagen sponge cylindrical scaffold prepared in Example 1 b) and from 88 to 92% for the hydroxyapatite coated collagen sponge cylinders obtained in Example 3 b).

The specific surface measured by mercury porosimetry was 2 $m^2/g$ for the collagen sponge cylindrical scaffold prepared in Example 1 b) and from 25 to 50 $m^2/g$ for the coated collagen sponge cylinders obtained in Example 3 b).

b) Mechanical Properties:

b1) Compressive Strength

The compressive strength (resistance to pressure), i.e. the maximum pressure to be applied for a compression of the cylinders to 50% of their original height, was measured using a mechanical compression test machine (Proline Z010 manufactured by Zwick/Roell).

The measured compressive strength in the wet state was from 0.3 to 0.7 MPa for the cylindrical pieces of fibrous collagen obtained in Example 1a) (varying the crosslinking conditions) and from 1.1 to 3.5 Mpa for the hydroxyapatite coated cylindrical pieces obtained in Example 3)a), the compressive strength increasing with the % of hydroxyapatite present in the hydroxyapatite coated cylindrical pieces.

b2) Resilience

The resilience, i.e. the % of original height recovered after compression to 50% or original height, was measured using a mechanical compression test machine (Proline Z010 manufactured by Zwick/Roell).

The measured resilience in the wet state was from 95 to 99% for the cylindrical pieces of fibrous collagen obtained in Example 1a) (varying the crosslinking conditions) and 92 to 100% for the hydroxyapatite coated cylindrical pieces obtained in Example 3)a), the % of hydroxyapatite present in those hydroxyapatite coated pieces appearing not to influence the resilience.

b3) Resistance to Torque

A protocol similar to the Straumann® Bone Block Fixation Method (cf. http://www.straumann.ch/ch-index/products/products-biologics/products-bone-block-fixation.htm) was used.

Briefly, using a driller to bore a 0.9 mm hole into a Teflon cylinder (having mechanical properties comparable to those of pig mandible bone) and into some the dried cylindrical pieces of fibrous collagen obtained in Example 1a) (varying the crosslinking conditions) and some of the dried hydroxyapatite coated cylindrical pieces obtained in Example 3)a), 2, and a magnetic screw driver (Klinge fTi Mikro Schr Kreuzschl, Ref. 75.23.19 available from Medicon) comprising a 1.5×12 mm screw, the maximum torque at which the cylindrical pieces could be screwed to the Teflon cylinder without breaking was measured.

All the tested uncoated cylindrical pieces of fibrous collagen obtained in Example 1a showed a resistance to torque of about 20 Ncm, whereas all of the tested hydroxyapatite coated cylindrical pieces obtained in Example 3)a) showed a resistance to torque of more than about 60 Ncm, the % of hydroxyapatite present in those hydroxyapatite coated pieces appearing not to influence the resistance to torque. A resistance to torque of about 30 Ncm is generally considered in the art as sufficient for screwing a piece to an osseous body part.

The dramatic increase in the resistance to torque is due to the strong epitactic binding between hydroxyapatite and the collagen scaffold.

Indeed, in comparative experiments performed on those crosslinked collagen scaffolds where according to conditions of the prior art hydroxyapatite was precipitated on or inside the collagen scaffold and thus weakly linked to the latter by adsorption, the resistance to torque was not significantly increased.

c) Hydroxyapatite Crystal Assembly Morphology as Determined by SEM

FIGS. 1 and 2 represent SEM micrographs of the fibrous side of the membrane-shaped collagen scaffold of Example 1c) coated as described in Example 3 b) with a PBS concentration of 0.2 M for a coating reaction time of 12 hours and O,8 M collagen for a coating time of 24 hours.

One can observe on FIG. 1 small hydroxyapatite crystal assemblies of finely distributed nano-sized crystal platelets with hexagonal symmetry closely interconnected with collagen fibrils and on FIG. 2 small micron-sized rosette-like aggregates of hexagonal hydroxyapatite crystal assemblies which completely covers the collagen fibre structure.

d) Assays of Colonization by Bone Forming Cells

It was shown on that the human MG63 osteoblast-like cells colonize with a high proliferation rate all sites of the coated membrane-shaped collagen scaffold obtained in Example 3 b). See FIG. 3.

In cytotoxicity tests the coated membrane-shaped collagen scaffold obtained in Example 3 b) showed results comparable to those obtained with the Bio-Gide® membrane.

The invention claimed is:

1. A biomimetic collagen-hydroxyapatite composite material comprising an at least partially fibrous collagen scaffold including mature native collagen fibers possessing triple helicity as shown by Circular Dichroism Spectroscopy, wherein those mature native collagen fibers are at least partially covered with epitactically grown crystals of nanocrystalline hydroxyapatite, whereby the epitactically grown nanocrystals have the same morphology as human bone mineral and the same size as human bone mineral, namely a length of 30 to 50 nm and a width of 14 to 25 nm and wherein the epitactically grown crystals of nanocrystalline hydroxyapatite form a layer having a thickness of at least 30±15 nm, as determined by X-ray diffraction analysis.

2. The biomimetic collagen-hydroxyapatite composite of claim 1, wherein the at least partially fibrous collagen scaffold comprises on its external surface at least 2% of mature native collagen fibers as determined by picture analysis on SEM micrographs and Circular Dichroism Spectroscopy.

3. The biomimetic collagen-hydroxyapatite composite of claim 1, wherein the at least partially fibrous collagen scaffold comprises on its external surface at least 10% of mature native collagen fibers as determined by picture analysis on SEM micrographs and Circular Dichroism Spectroscopy.

4. The biomimetic collagen-hydroxyapatite composite material of claim 1 wherein the fibrous collagen scaffold has a w/w ratio to the epitactically grown crystals of nanocrystalline hydroxyapatite between 5:95 and 95:5.

5. The biomimetic collagen-hydroxyapatite composite material of claim 1 which is a shaped body.

6. The biomimetic collagen-hydroxyapatite composite material of claim 5, wherein the shaped body is a bone substitute material the structure of which has the profile of an osseous body part.

7. The biomimetic collagen-hydroxyapatite composite material of claim 5, wherein the shaped body has a resistance to torque of at least 30 Ncm in the dry state.

8. The biomimetic collagen-hydroxyapatite composite material of claim 1 which is membrane-shaped.

9. A process of preparing the biomimetic collagen-hydroxyapatite composite material of claim 1, the process comprising the steps of:
   a) immersing an at least partially fibrous collagen scaffold including mature native collagen fibers possessing triple helicity as shown by Circular Dichroism Spectroscopy in a saturated aqueous solution of saturated $Ca^{2+}/H_xPO_4^{(3-x)}$, which is a phosphate buffer solution (PBS) containing finely dispersed alpha-TCP, beta-TCP, TTCP, octacalcium phosphate pentahydrate, dicalcium phosphate or dicalcium phosphate dihydrate, to perform the formation process of the composite implant material whereby epitactically grown hydroxyapatite nanocrystals are formed on those mature native collagen fibers, those epitactically grown hydroxyapatite nanocrystals having the same morphology and same size as human bone mineral, namely a length of 30 to 50 nm and a width of 14 to 25 nm and wherein the epitactically grown crystals of nanocrystalline hydroxyapatite form a layer having a thickness of at least 30±15 nm, as determined by X-ray diffraction analysis, b) stopping the formation process of the composite implant material by separating solid material from the aqueous solution, rinsing with water and drying, and c) optionally sterilizing the separated material coming from step b).

10. The process of claim 9 wherein in step a) the pH of the aqueous solution remains within a range of 5.5 to 9.0.

11. The process of claim 9 wherein in step a) the pH of the aqueous solution remains within a range of 6.5 to 8.0.

12. The process claim 9 wherein the temperature in step a) is between 25 and 45° C.

13. The process of claim 9 wherein the temperature in step a) is between 35° C. and 42° C.

14. The biomimetic collagen-hydroxyapatite composite material of claim 1, in the form of an implant or prosthesis for bone formation, bone regeneration, bone repair and/or bone replacement at a defect site in a human subject or an animal.

15. The membrane-shaped biomimetic collagen-hydroxyapatite composite material according to claim 8, in the form of an implant for combined bone and cartilage regeneration.

16. A method of promoting bone formation, bone regeneration and/or bone repair at a defect site in a human subject or an animal comprising implanting the biomimetic collagen-hydroxyapatite composite material of claim 1 in said human subject or animal.

17. The biomimetic collagen-hydroxyapatite composite material of claim 4, wherein the w/w ratio is between 10:90 and 90:10.

* * * * *